[54] 1-METHYL-2,3-DIHYDRO-1,4-DITHIINIUM METHOSULFATE

[75] Inventors: Klaus Naumann, Cologne; Klaus Lürssen, Groszkoenigsdorf; Klaus Sasse, Schildgen, all of Germany

[73] Assignee: Bayer Aktiengesellschaft, Leverkusen, Germany

[22] Filed: June 5, 1974

[21] Appl. No.: 476,765

[30] Foreign Application Priority Data

June 19, 1973 Germany............................ 2331186

[52] U.S. Cl. ................................ 260/327 P; 71/90
[51] Int. Cl.² ........................................ C07D 339/08
[58] Field of Search................................ 260/327 P

[56] References Cited
UNITED STATES PATENTS
2,965,649  12/1960  Johnston............................ 260/327

OTHER PUBLICATIONS
Schroth, et al., Z. Chem. 1970, 10(8), pp. 296–297 [cited as Chem. Abs. 73:114791w–1970].

*Primary Examiner*—Natalie Trousof
*Assistant Examiner*—C. M. S. Jaisle
*Attorney, Agent, or Firm*—Burgess, Dinklage & Sprung

[57] ABSTRACT

1,4-dithiene sulfonium salts of the formula

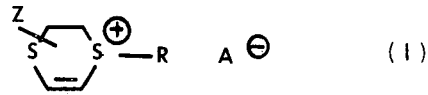

in which
R is alkyl, substituted alkyl, alkenyl, alkynyl of up to 8 carbon atoms; cycloalkyl, aralkyl; or aralkyl substituted in the aryl moiety;
Z is hydrogen or alkyl, and
A⁻ is one equivalent of an anion
are outstandingly effective as plant growth regulants, e.g., as plant growth inhibitors.

1 Claim, No Drawings

1-METHYL-2,3-DIHYDRO-1,4-DITHIINIUM METHOSULFATE

The present invention relates to certain new sulfonium salts of 1,4-dithiene compounds, to plant growth regulant compositions containing them and to their use for regulating plant growth.

It is known that certain 2-halogenoethyl-trialkylammonium salts, especially (2-chloroethyl)-trimethylammonium chloride, display plant-growth regulating properties from U.S. Pat. No. 3,156,544. However, the action of these compounds is not always satisfactory, especially if low amounts and concentrations are used.

The present invention provides, as new compounds, the 1,4-dithiene-sulfonium salts of the formula

(I)

in which
R is alkyl, substituted alkyl, alkenyl, alkynyl of up to 8 carbon atoms; cycloalkyl; aralkyl; or aralkyl substituted in the aryl moiety;
Z is hydrogen or alkyl, and
$A^\ominus$ is one equivalent of an anion.

The salts of the formula (I) have been found to display strong plant-growth-regulating properties. Surprisingly, the present sulfonium salts of 1,4-dithienes display a substantially greater plant-growth-regulating action than the known compound (2-chloroethyl)-trimethylammonium chloride which is chemically the nearest active compound of the same type of action. The compounds according to the invention thus represent a valuable enrichment of the art.

Preferably, R is optionally substituted straight-chain or branched alkyl of from 1 to 4 carbon atoms (preferred substituents being hydroxyl, methoxy, methylcarbonyl, alkoxycarbonyl of from 1 to 4 carbon atoms in the alkyl moiety and halogen, especially chlorine and bromine), alkenyl of from 2 to 4 carbon atoms, alkynyl of from 2 to 4 carbon atoms, cycloalkyl of from 3 to 12 carbon atoms, especially 3 to 7 carbon atoms, or aralkyl of from 1 to 4 carbon atoms in the alkyl moiety and 6 to 10 carbon atoms in the aryl moiety, which aryl moiety is optionally substituted by halogen, for example chlorine; Z is hydrogen or straight-chain or branched alkyl of from 1 to 4 carbon atoms; and $A^-$ is chloride, bromide, iodide or a methylsulfate, ethylsulfate or tetrafluoborate ion.

The present invention also provides a process for the preparation of a 1,4-dithiene-sulfonium salt of the formula (I), in which a 1,4-dithiene of the formula

(II)

in which
Z has the above-mentioned meaning, is reacted with a compound of the formula $$R' - X \qquad (III)$$

in which
R' is optionally substituted alkyl, alkenyl, alkynyl, cycloalkyl, aralkyl which is optionally substituted in the aryl moiety, or the triethyloxonium ion, and
X is halogen, akylsulfate or tetrafluoborate, optionally in the presence of a solvent, at a temperature between 0°C and 130°C, and optionally - if the anion in the compound prepared is chloride, bromide or iodide - the anion is exchanged by subsequent treatment with a silver salt. The anion exchange can also be achieved by using an anion exchange resin.

X is preferably chlorine, bromine, iodine, methylsulfate, ethylsulfate, or the tetrafluoborate ion.

If 1,4-dithiene and dimethyl sulfate are used as starting materials, the course of the reaction can be represented by the following equation:

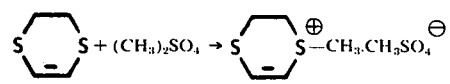

The 1,4-dithienes of the formula (II) which can be used according to the invention are already known (see J. Amer. Chem. Soc. 77, 1169-1174 (1955), and U.S. Patent Specification 3,439,051). The following may be mentioned as examples thereof: 1,4-dithiene, 2-methyl-1,4-dithiene-2, 2-ethyl-1,4-dithiene-2, 2-propyl-1,4-dithiene-2, 2-n-butyl-1,4-dithiene-2, 2-isobutyl-1,4-dithiene-2 and 5-methyl-1,4-dithiene-2.

The compounds of the formula (III) which can be used as starting materials are already known. The following may be mentioned as examples thereof; methyl iodide, ethyl bromide, propyl chloride, allyl chloride, propargyl chloride, benzyl chloride, 4-chlorobenzyl chloride, 2,4-dichlorobenzyl chloride, chloroacetone, chloroacetic acid and its esters, chloromethyl ether, chloromethylnaphthalene, dimethyl sulfate, diethyl sulfate and triethyloxonium tetrafluoborate.

Solvents which can be used in carrying out the reaction according to the invention include lower alcohols, preferably methanol, and chlorinated hydrocarbons, preferably chloroform or methylene chloride, as well as dimethylformamide, acetonitrile acetone, dioxane or water.

The reaction temperatures can be varied over a fairly wide range. In general, the reaction is carried out at between 0°C and 130°C, preferably between 20°C and 120°C.

The reactions are in general carried out under normal pressure.

In carrying out the process according to the invention, preferably 1 mole of the starting compound of the formula (II) is reacted per mole of the reactant of the formula (III).

In the preparation of the compounds according to the invention by the above process, the reaction products are either obtained directly in a crystalline form after completion of the reaction or can, after completion of the reaction, be separated out in an oily or crystalline state by addition of a solvent in which they are insoluble. The crystalline products are isolated - if necessary after prior concentration of the reaction mixture - by simple filtration. Additional purification can be achieved by reprecipitation. If the reaction products are obtained as oils, they are isolated by first separating the phases and purifying the oil by treatment with active charcoal in aqueous or alcoholic solution.

In the reaction employing the compound (III), only those compounds of the formula (I) in which the anion A⁻ denotes halide, alkylsulfate or tetrafluoborate are initially produced. However, if subsequently a compound of the formula (I) in which A represents chloride, bromide or iodide is reacted with a silver salt, the halide can be replaced by the anion of the silver salt. The halide can also be replaced by a great variety of anions by using the anion exchange technique via anion exchange resin.

The preparation of the compounds of the invention is illustrated by the following Example.

Example 1

Preparation of 1-methyl-sulfonia-4-thiacyclohexene(2) methosulfate

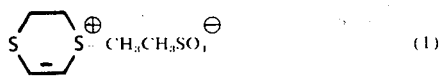

11.8 g (0.1 mole) of 1,4-dithiacyclohexene and 12.6 g (0.1 mole) of dimethyl sulfate were mixed at 20°C and left to stand for several days at room temperature. The crystals which had separated out were then filtered off and washed with ether to purify them further. 11 g (45% of theory) of 1-methyl-sulfonia-4-thiacyclohexene-(2) methosulfate were obtained in the form of colorless crystals of melting point 88°C.

Analysis

Calculated: for $C_6H_{12}O_4S_3$ 29.5% C, 4.9% H, 39.4% S
Found: 29.0% C, 4.8% H, 40.1% S The active compounds according to the invention affect the physiological metabolism of plant growth and can therefore be used as plant-growth regulators.

The diverse effects of the active compounds depend essentially on the point in time at which they are used, relative to the stage of development of the seed or of the plant, and on the concentrations used.

Plant-growth regulators are used for various purposes which are related to the stage of development of the plant.

The growth of the plants can be greatly inhibited by means of the compounds according to the invention. Such inhibition of vegetative growth plays an important role in cereals since this can reduce or completely prevent lodging.

At the same time, the compounds according to the invention achieve a strengthening of the stalk.

In the case of many crop plants, inhibition of the vegetative growth permits denser planting of the crop so that an increased yield relative to soil area can be achieved. A further mechanism of increasing the yield by means of growth inhibitors is based on the fact that the nutrients benefit blossoming and fruiting to an increased extent while vegetative growth is restricted.

However, a promotion of vegetative growth can also be achieved with the compounds according to the invention. This is of great value where it is the vegetative parts of the plants which are harvested. However, promotion of vegetative growth can at the same time also lead to promotion of generative growth so that, for example, more fruit or larger fruit, is formed.

Further, the active compounds according to the invention can be used to accelerate or retard the ripening of fruit and to improve the color of fruit. It is also possible to concentrate the ripening of the fruit within a shorter time. The desired effects can be achieved by varying the concentrations of the active compounds employed and by applying them at different times during the development of the plant.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquefied gaseous diluents or carriers, optionally with the use of surface-active agents, that is, emulsifying agents and/or dispersing agents and/or foam-forming agents. In the case of the use of water as an extender, organic solvents can, or example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexane, or strongly polar solvents, such as dimethyl formamide, dimethyl sulfoxide or acetonitrile, as well as water.

By liquefied gaseous diluents or carriers are meant liquids which would be gaseous at normal temeratures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying and foam-forming agents include non-ionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates as well as albumin hydrolyzation products; and preferred examples of dispersing agents include lignin sulfite waste liquors and methyl cellulose.

The active compounds according to the invention can be present in the formulations as a mixture with other active compounds.

The formulations in general contain from 0.1 to 95 per cent by weight of active compounds, preferably from 0.5 to 90 per cent.

The active compounds can be used as such, as their formulations or as the application forms prepared therefrom, such as ready-to-use solutions, emulsions, foams, suspensions, powders, pastes and granules. They may be used in the customary manner, for example by watering, spraying, atomizing, scattering, dusting, seed treating and the like.

The concentrations of active compound can be varied within a fairly wide range. In general, concentrations from 0.0005 to 2%, preferably from 0.01 to 0.5%, by weight are used.

Furthermore, 0.1 to 100 kg, preferably 1 to 10 kg, of active compound are, in general, used per hectare of soil area.

The preferred period of time at which the growth regulators are used depends on the climatic and vegetative circumstances.

The present invention also provides a plant-growth-regulating composition containing as active ingredient a salt of the present invention in admixture with a solid or liquefied gaseous diluent or carrier or in admixture with a liquid diluent or carrier containing a surface-active agent.

The present invention also provides a method of regulating the growth of plants, which comprises applying to the plants or a plant habitat a salt of the present invention alone or in the form of a composition containing as active ingredient a salt of the present invention in admixture with a diluent or carrier.

The present invention further provides methods of obtaining plants, the growth of which has been regulated by their being grown in areas in which immediately prior to and/or during the time of the growing a salt of the present invention was applied alone or in admixture with a diluent or carrier. It will be seen that the usual methods of providing a harvested crop may be improved by the present invention.

In the test Example which follows, the activity of the compounds according to the invention as growth regulators is illustrated without excluding the possibility of further uses as growth regulators.

Example A

Inhibition of growth/wheat

Solvent: 10 parts by weight of methanol Emulsifier: 2 parts of polyethylene sorbitan monolaurate To prepare a suitable preparation of active compound, 1 part by weight of active compound was mixed with the stated amount of solvent and emulsifier and the mixture was made up to the desired concentration with water.

Young wheat plants, 25–30 cm high, were sprayed with the preparation of active compound until dripping wet. After four weeks, the additional growth was measured and the inhibition of growth in % of the additional growth of the control plants was calculated. 100% means that growth had stopped and 0% denotes a growth corresponding to that of the untreated plants.

The active compounds, active-compound concentrations and results can be seen from the table which follows:

Table A

| Active compound | Inhibition of growth/wheat Concentration in ppm | Inhibition of growth in % |
|---|---|---|
| Water (control) | — — | 0 |
| 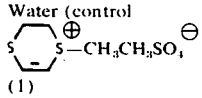 (1) | 500 | 40 |

It will be understood that the specification and examples are illustrative but not limitative of the present invention and that other embodiments within the spirit and scope of the invention will suggest themselves to those skilled in the art.

What is claimed is:

1. 1methyl-2,3-dihydro-1,4-dithiinium methosulfate.

* * * * *